(12) United States Patent
Cork et al.

(10) Patent No.: US 9,816,073 B2
(45) Date of Patent: Nov. 14, 2017

(54) SYSTEMS AND METHODS FOR DETECTING FLUID LEAKS USING A NON-CONTACT SENSOR

(71) Applicant: Fenwal, Inc., Lake Zurich, IL (US)

(72) Inventors: William H. Cork, Mettawa, IL (US); Gregory G. Pieper, Spring Grove, IL (US); Katherine N. Radwanski, Des Plaines, IL (US); Salvatore Manzella, Jr., Barrington, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 14/810,058

(22) Filed: Jul. 27, 2015

(65) Prior Publication Data
US 2017/0029776 A1 Feb. 2, 2017

(51) Int. Cl.
| | |
|---|---|
| *C12N 5/078* | (2010.01) |
| *A61M 1/36* | (2006.01) |
| *A61L 2/08* | (2006.01) |
| *C12M 1/12* | (2006.01) |
| *C12M 1/36* | (2006.01) |
| *A61L 2/00* | (2006.01) |
| *A61M 1/02* | (2006.01) |

(52) U.S. Cl.
CPC .......... *C12N 5/0641* (2013.01); *A61L 2/0047* (2013.01); *A61M 1/0209* (2013.01); *A61M 1/3681* (2013.01); *A61M 1/3683* (2014.02); *A61M 1/3696* (2014.02); *C12M 37/00* (2013.01); *C12M 41/48* (2013.01); *A61L 2202/14* (2013.01); *A61L 2202/22* (2013.01); *A61M 2205/051* (2013.01); *A61M 2205/12* (2013.01); *A61M 2205/15* (2013.01); *A61M 2205/3306* (2013.01)

(58) Field of Classification Search
None
See application file for complete search history.

(56) References Cited

U.S. PATENT DOCUMENTS

| | | | |
|---|---|---|---|
| 5,360,542 A | 11/1994 | Williamson, IV et al. | |
| 6,027,657 A | 2/2000 | Min et al. | |
| 7,433,030 B2 | 10/2008 | Waldo et al. | |
| 2002/0192632 A1 | 12/2002 | Hei et al. | |
| 2006/0221329 A1* | 10/2006 | Waldo | A61L 2/0011 356/213 |
| 2012/0195791 A1 | 8/2012 | Schmidt et al. | |
| 2013/0155138 A1* | 6/2013 | Batchelor | B41J 29/02 347/17 |
| 2014/0370491 A1 | 12/2014 | Radwanski | |

FOREIGN PATENT DOCUMENTS

| | | |
|---|---|---|
| WO | WO 2009/005853 | 1/2009 |
| WO | WO 2009/115774 | 9/2009 |
| WO | WO 2010/132167 | 11/2010 |
| WO | WO 2011/045243 | 4/2011 |

OTHER PUBLICATIONS

Partial International Search, counterpart PCT Appl. No. PCT/US2016/043147 (Nov. 9, 2016).
International Search Report and Written Opinion, counterpart PCT Appl. No. PCT/US2016/043147 (Jan. 18, 2017).

* cited by examiner

*Primary Examiner* — Michelle F Paguio Frising
(74) *Attorney, Agent, or Firm* — Cook Alex Ltd.

(57) ABSTRACT

An irradiation device includes a fluid treatment chamber configured to receive a biological fluid container, the fluid treatment chamber having opposing first and second sides, at least one light source disposed adjacent at least one of the first and second sides of the fluid treatment chamber, and an overflow reservoir in fluid communication with the fluid treatment chamber to receive fluid leaking from the biological fluid container. The device also includes a non-contact sensor disposed adjacent the overflow reservoir and configured to generate a signal according to leaked fluid in the overflow reservoir, an indicator, and a controller coupled to the at least one light source, the non-contact sensor and the indicator, the controller configured to activate the indicator upon receipt of the signal from the sensor and to deactivate the at least one light source subsequent to receipt of the signal from the sensor.

20 Claims, 7 Drawing Sheets

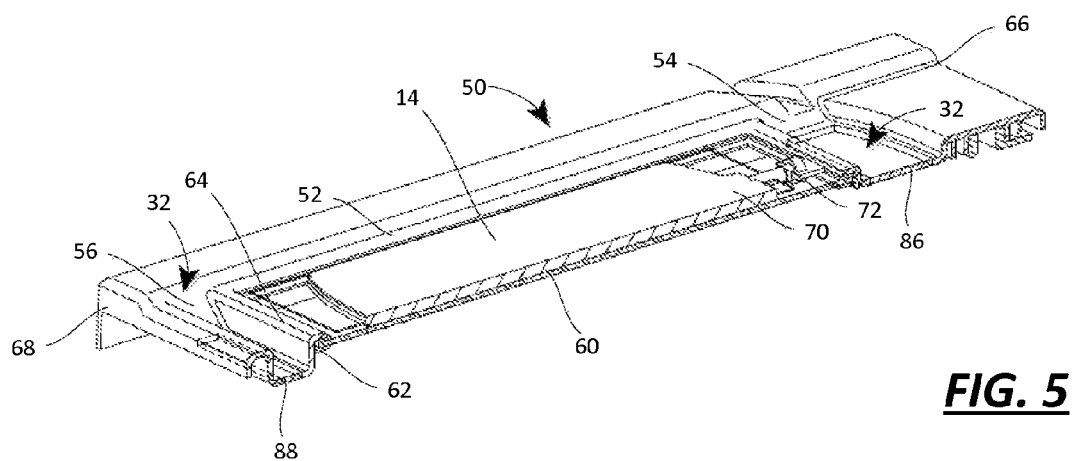
*FIG. 5*
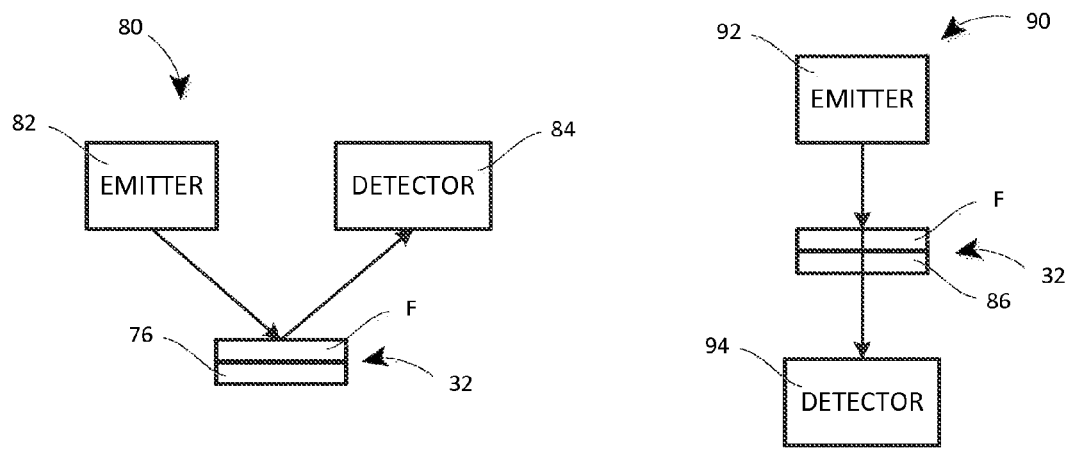
*FIG. 6*
*FIG. 7*

SYSTEMS AND METHODS FOR DETECTING FLUID LEAKS USING A NON-CONTACT SENSOR

BACKGROUND

Field of the Disclosure

This patent relates to devices, methods and systems for processing and treating biological fluids, such as blood and blood components. More particularly, the patent relates to devices, methods and systems involving irradiation of biological fluids, such as blood and blood components, in a container disposed in a treatment chamber.

Description of Related Art

An irradiation device is particularly useful in the treatment of biological fluids. As used herein, biological fluid refers to any fluid that is found in or that may be introduced into the body including, but not limited to, blood and blood products. As used herein, "blood product" refers to whole blood or a component of whole blood such as red blood cells, white blood cells, platelets, plasma or a combination of one or more of such components that have been separated from whole blood.

For example, an irradiation device may be used in the treatment of a blood product that has been combined with a photochemical agent for activation when subjected to light. Such photochemical agents are used, for example, in the inactivation of viruses, bacteria, and other contaminants (collectively referred to herein as "pathogens"). Photochemical agents are also used in the treatment of mononuclear cells, such as white blood cells. In pathogen inactivation applications, the activated agent inactivates pathogens that may be present in a blood product. In the treatment of mononuclear cells, the activated agent targets the mononuclear cell itself as part of a treatment of a disease or a side effect of a mononuclear cell therapy.

Typically, the biological fluid to be treated is introduced into a fluid treatment chamber within the irradiation device in flexible, plastic, sterilizable, translucent, biologically compatible containers. The containers may be integrally connected to other containers and plastic tubing useful in the processing of the biological fluid both before and after the treatment provided by the irradiation device.

One such irradiation device is described in U.S. Pat. No. 7,433,030. The device includes a fluid carrying drawer with a central cavity to allow for placement of a container-carrying tray. The tray is described as having a volume sufficient to hold at least the entire volume of biological fluid contained within the containers so as to minimize the risk that, in the event of container leakage, liquid will overflow and contact the electrical and mechanical components of irradiation device, even during agitation.

SUMMARY

There are several aspects of the present subject matter that may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In a first aspect, an irradiation device comprises a fluid treatment chamber configured to receive a biological fluid container, the fluid treatment chamber having opposing first and second sides, at least one light source disposed adjacent at least one of the first and second sides of the fluid treatment chamber, and an overflow reservoir in fluid communication with the fluid treatment chamber to receive fluid leaking from the biological fluid container. The irradiation device further comprises a non-contact sensor disposed adjacent the overflow reservoir configured to generate a signal according to leaked fluid in the overflow reservoir, an indicator, and a controller coupled to the at least one light source, the non-contact sensor and the indicator, the controller configured to activate the indicator upon receipt of the signal from the sensor and to deactivate the at least one light source subsequent to receipt of the signal from the sensor.

In another aspect, a method of controlling an irradiation device comprises Illuminating a biological fluid container in a fluid treatment chamber, sensing biological fluid from the fluid container in overflow reservoir in fluid communication with the fluid treatment chamber using a non-contact sensor, activating an indicator after sensing the biological fluid in the overflow reservoir, and deactivating illumination of the biological fluid container subsequent to sensing the biological fluid in the overflow reservoir.

In a further aspect, a system comprises a cell separator configured to direct a biological fluid into a biological fluid container and an irradiation device. The irradiation device comprises a fluid treatment chamber configured to receive the biological fluid container, the fluid treatment chamber having opposing first and second sides, at least one light source disposed adjacent at least one of the first and second sides of the fluid treatment chamber, and an overflow reservoir in fluid communication with the fluid treatment chamber to receive fluid leaking from the biological fluid container. The irradiation device further comprises a non-contact sensor disposed adjacent the overflow reservoir configured to generate a signal according to leaked fluid in the overflow reservoir, an indicator, and a controller coupled to the at least one light source, the non-contact sensor and the indicator, the controller configured to activate the indicator upon receipt of the signal from the sensor and to deactivate the at least one light source subsequent to receipt of the signal from the sensor.

BRIEF DESCRIPTION OF THE DRAWINGS

FIG. 5 is a cross-sectional, perspective view of another embodiment of a tray for use with the irradiation device of FIG. 1.

FIG. 6 is a schematic diagram of an embodiment of a sensor for use with the embodiment of tray illustrated in FIGS. 3 and 4.

FIG. 7 is a schematic diagram of an embodiment of a sensor for use with the embodiment of tray illustrated in FIG. 5.

DESCRIPTION OF THE ILLUSTRATED EMBODIMENTS

The embodiments disclosed herein are for the purpose of providing an exemplary description of the present subject matter. They are, however, only exemplary, and the present subject matter may be embodied in various forms. Therefore, specific details disclosed herein are not to be interpreted as limiting the subject matter as defined in the accompanying claims.

Figure 1:
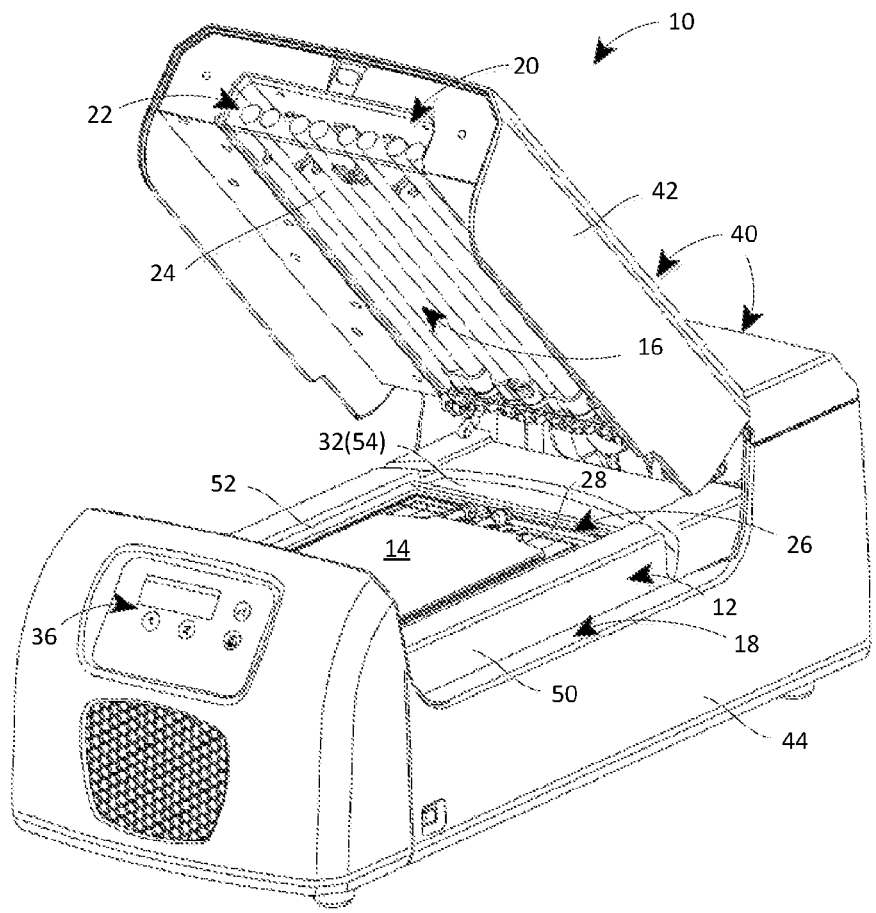
FIG. 1 is a perspective view of an embodiment of a device used to irradiate a collection of cells in a biological fluid container disposed on a tray.
Figure 2:
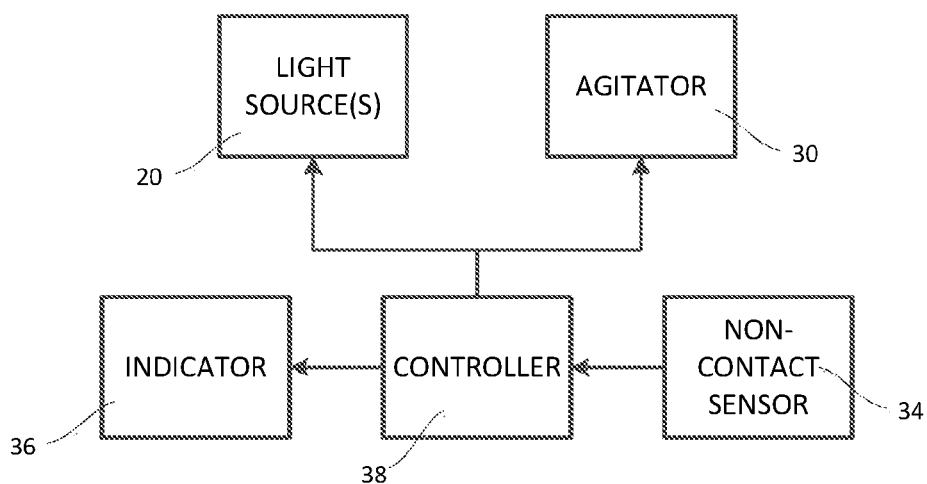
FIG. 2 is a block diagram of an embodiment of the electronic components of the irradiation device of FIG. 1.

As illustrated in FIG. 1, an irradiation device 10 includes a fluid treatment chamber 12 configured to receive a biological fluid container 14, fluid treatment chamber 12 having opposing first and second sides 16, 18. As illustrated in FIGS. 1 and 2, device 10 also includes at least one light source 20 disposed adjacent at least one of first and second sides 16, 18 of fluid treatment chamber 12. Light source 20 may include, for example, a first array 22 with a plurality of light sources 24 disposed on first side 16 of fluid treatment chamber 12 and a second array 26 with a plurality of light sources 28 disposed on second side 18 of fluid treatment chamber 12. According to an embodiment of the present disclosure, light sources 26, 28 are similar in structure and operation, and provide electromagnetic radiation in the ultraviolet portion of the spectrum (e.g., UVA). An alternative device is described in U.S. Pat. No. 7,433,030, the contents of which is incorporated by reference herein in its entirety.

As is also illustrated in FIG. 2, device 10 may include an agitator 30 coupled to fluid treatment chamber 12 to move at least a part of fluid treatment chamber 12 with an oscillatory motion. Agitator 30 may include a motor in combination with a linkage (such as a rotating cam), the linkage coupling the motor to fluid treatment chamber 12. An embodiment of an agitator is described in the aforementioned U.S. Pat. No. 7,433,030, which has been incorporated herein. Agitator 30 may cause fluid treatment chamber 12, or at least biological fluid container 14 disposed in fluid treatment chamber 12, to move in an oscillatory fashion over a distance of 2.54 cm (1 inch) at a frequency of 1 Hz according to one such embodiment.

Device 10 also includes an overflow reservoir 32 in fluid communication with fluid treatment chamber 12 to receive fluid leaking from biological fluid container 14. While overflow reservoir 32 solves the problem of confining any leakage of fluid from container 14, and preventing damage to the remainder of device 10, overflow reservoir 32 presents a separate issue in that the operator cannot tell that container 14 has leaked until overflow reservoir 32 is visually inspected at the end of an operational cycle. If container 14 has leaked, it may be necessary to dispose of container 14 and its contents as waste, and begin the procedure anew. This can lead to a considerable wastage of time, both for the patient and the operator. On the other hand, if a leak can be detected before the cycle has been completed, then operation of device 10 may be terminated before the typical completion of the cycle, resulting in a savings of time, both for the patient and the operator, relative to the usual outcome.

A non-contact sensor 34 (see FIGS. 2, 6, and 7) is disposed adjacent to, but not in contact with, overflow reservoir 32 and is configured to generate a signal according to leaked fluid in the overflow reservoir 32. According to different embodiments, a single non-contact sensor 34 may be provided for overflow reservoir 32, or a plurality of non-contact sensors 34 may be provided. In particular, where overflow reservoir 32 is large or is defined by volumes separated spatially from each other, a plurality of non-contact sensors 34 may be included, one for each of the separate volumes, for example. Non-contact sensor 34 may an optical sensor, for example, although other forms of non-contact sensor may be utilized as well.

Irradiation device 10 also includes an indicator 36 (such as a light, for example) and a controller 38 (see FIGS. 1 and 2). Controller 38 is coupled to light source 20, non-contact sensor 34 and indicator 36. Controller 38 may be coupled to light source 20, non-contact sensor 34 and indicator 36 directly, or light source 20, non-contact sensor 34 and indicator 36 may be coupled to controller 38 through other intermediary equipment, such as signal processing equipment in the case of the sensor 34. Light source 20, non-contact sensor 34 and indicator 36 may have their own power source, or they may share a power source with the controller 38 or be powered through the controller 38.

Controller 38 is configured to activate indicator 36 upon receipt of the signal from sensor 34 and to deactivate light source 20 subsequent to receipt of signal from sensor 34. Where device 10 includes agitator 30, controller 38 may be coupled to agitator 30, and may be configured to deactivate agitator 30 subsequent to receipt of the signal from sensor 34.

Device 10 may also include a housing 40 in which fluid treatment chamber 12 is defined, and in which light source 20, agitator 30, overflow reservoir 32, and non-contact sensor 34 are disposed. Controller 38 may also be disposed in housing 40, while indicator 36 may be disposed on or outside the housing 40 so as to be visible to the operator. While FIG. 1 illustrates an embodiment of housing 40 including a lid 42 that may be moved pivotally relative to a base 44 to open housing 40 and permit access to fluid treatment chamber 12, it will be recognized that according to other embodiments of device 10, housing 40 may instead include a sliding drawer that permits access to fluid treatment chamber 12.

Device 10 according to FIGS. 1 and 2 may be operated as follows. Light source 20 may be activated, thereby illuminating biological fluid container 14 in fluid treatment chamber 12. According to certain embodiments, agitator 30 may also be activated, thereby agitating biological fluid container 14 while biological fluid container 14 is illuminated. If the biological fluid leaks from container 14, non-contact sensor 34 may be used to sense the biological fluid flowing from fluid container 14 into overflow reservoir 32. Controller 38 may then activate indicator 36 upon receipt of a signal from the sensor 34. Illumination of biological fluid container 14 may be deactivated subsequent to sensing the biological fluid in overflow reservoir 32, as may agitation of biological fluid container 14. According to certain embodiments, controller 38 may deactivate the illumination and agitation of biological fluid container 14 automatically upon receipt of a signal from non-contact sensor 34.

In this fashion, the non-contact sensor 34 may be used to terminate operation of device 10 when a leak occurs, limiting wastage of time and equipment as a consequence.

Non-contact sensor 34 is particularly desirable where agitator 30 is included in device 10, and overflow reservoir 32 is moved by agitator 30. If a sensor that was in contact with overflow reservoir 32 was used to detect the presence of fluid in reservoir 32, then it would be necessary to address the motion of reservoir 32, which as described above may be at a frequency of 1 Hz over a distance of 2.54 cm (1 inch). With the use of a non-contact sensor, the effect of the motion of the reservoir on the sensor and its connections to other components is limited. It will be recognized, however, that use of non-contact sensor 34 also may facilitate the cleaning and possible removal of reservoir 32, even if agitator 30 is not included as part of device 10.

Having described the general structure and operation of irradiation device 10, the details of the structure and operation now may be discussed.

Figure 3:
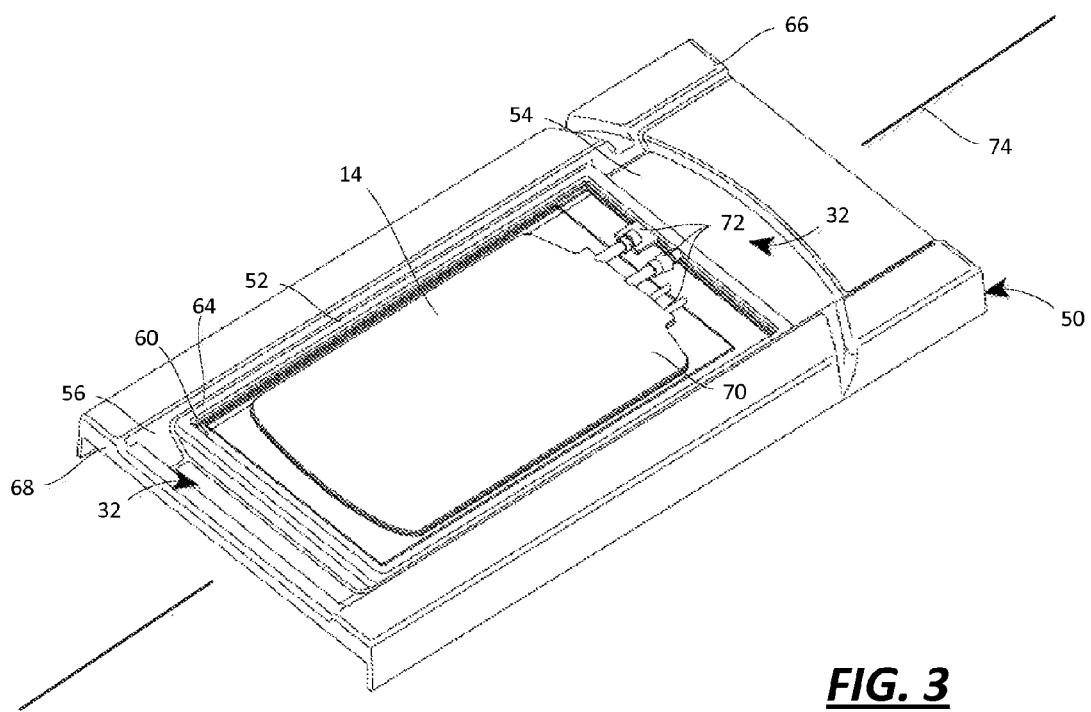
FIG. 3 is a top perspective view of an embodiment of a tray for use with the irradiation device of FIG. 1.
Figure 4:
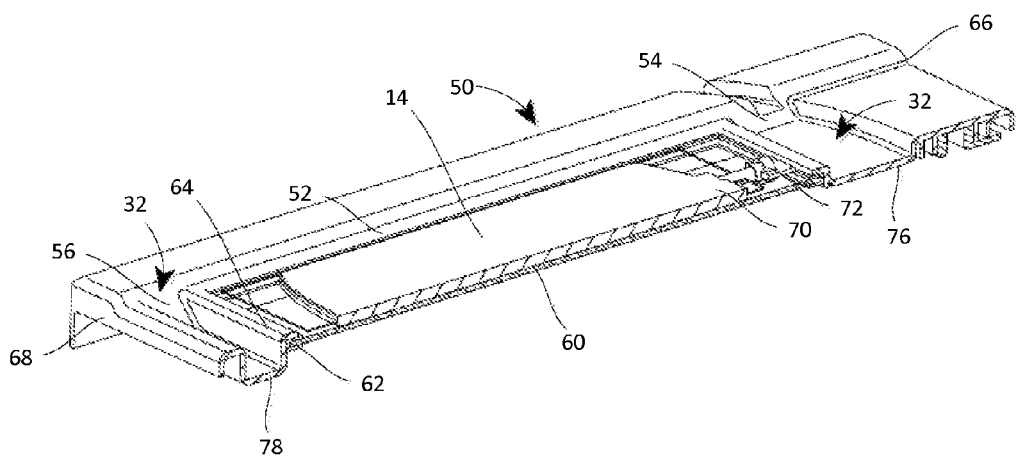
FIG. 4 is a cross-sectional, perspective view of the tray of FIG. 3.

As illustrated, in FIG. 1, fluid treatment chamber 12 may be defined, at least in part, by a tray 50 (housing 40 may also assist in defining fluid treatment chamber 12). A first embodiment of tray 50 is illustrated in FIGS. 3 and 4, while a second embodiment of tray 50 is illustrated in FIG. 5. Tray 50 may be made of a polymeric material in part, with certain sections of tray 50 made of another material, such as glass.

According to either embodiment, tray 50 has a first recess or pocket 52 that defines fluid treatment chamber 12. Tray 50 may have one or more additional recesses or pockets 54, 56 that define, at least in part, overflow reservoir 32. The illustrated embodiments include two additional recesses 54, 56; this does not exclude the possibility that other embodiments may include only a single additional recess or may include more than two additional recesses.

First recess 52 has a translucent floor 60 (see FIGS. 4 and 5). Floor 60 is translucent to permit the illumination of biological fluid container 14 on both sides, for example, where, as here, light source 20 includes plurality of light sources 24, 28 arranged in one or more arrays 22, 26 disposed on either side of tray 50, and thus either side 16, 18 of fluid treatment chamber 12. Floor 60 may be made of glass, for example, disposed in a frame 62 that is attached or secured to the remainder of tray 50. In an embodiment of irradiation device 10 where container 14 is illuminated on only one side, floor 60 may be non-translucent.

First recess 52 is defined by a rim or lip 64 disposed about the periphery of recess 52. The rim or lip 64 is useful in limiting the motion of container 14 relative to tray 50, to ensure that container 14 is adequately illuminated. According to the illustrated embodiment, first recess 52 is disposed approximately at the middle or center of tray 50, between opposing first and second ends 66, 68 of tray 50. While rim or lip 64 may be high enough to limit the motion of container 14 relative to tray 50, rim or lip 64 is not high enough to define a volume that would accept the entire contents of container 14, or to prevent the movement of leaking or leaked fluid out of first recess 52, particularly if agitator 30 is included and operational.

As noted above, tray 50 may include at least one recess 54, 56 in addition to first recess 52. According to the embodiment illustrated in FIGS. 3 and 4 and the embodiment illustrated in FIG. 5, tray 50 includes second recess 54 and third recess 56. Second recess 54 is disposed at first end 66 of tray 50 nearer to an end 70 of container 14 having ports 72 for accessing the contents of container 14. Third recess 56 is disposed at second end 72 of tray 50 further from port end 70 of container 14. Together, second and third recesses 54, 56 define overflow reservoir 32. For those embodiments where a single recess defines overflow reservoir 32, the single recess may be, for example, second recess 54 illustrated in the embodiment of FIGS. 3 and 4 or that of FIG. 5.

Rim or lip 64 separates first recess 52 from second recess 54 and third recess 56, but does not prevent fluid communication between first, second and third recesses 52, 54, 56. This is particularly true where tray 50 is agitated while container 14 is illuminated, the agitation occurring as a consequence of an oscillatory motion applied to tray 50 along a longitudinal axis 74 of tray 50. The motion of tray 50 back and forth along longitudinal axis 74 may cause fluid to move up and over rim 64, and into second and/or third recess 54, 56.

According to the embodiment of FIGS. 3 and 4, second and third recesses 54, 56 have a non-translucent floor 76, 78. This particular embodiment of the tray may be used with one or more non-contact sensors 34 in the form of an optical sensor, and in particular one or more reflective light sensors 80, an example of which is illustrated in the diagram of FIG. 6.

Reflective light sensor 80 of FIG. 6 includes a light emitter 82 and a light detector 84. Light emitter 82 and light detector 84 are both disposed on one side of overflow reservoir 32 (e.g., mounted on, in or to lid 42). A light beam (illustrated in the form of an arrow) is emitted from emitter 82 and is at least partially reflected off the floor (e.g., floor 76) or the fluid F and sensed by the detector 84. Optical sensor 80 may provide a signal to controller 38 when any amount of fluid is present in reservoir 32, or when a particular height of fluid is contained in the reservoir 32.

According to the embodiment of FIG. 5, second and third recesses 54, 56 have a translucent floor 86, 88. This particular embodiment of tray 50 may be used with one or more non-contact sensors 34 in the form of an optical sensor, and in particular one or more light absorption sensor 90, an example of which is illustrated in the diagram of FIG. 7.

Light absorption sensor 90 of FIG. 7 also includes a light emitter 92 and a light detector 94. However, light emitter 90 and light detector 94 are disposed on opposite sides of overflow reservoir 32 (e.g., one may be mounted on, in or to lid 42 and the other may be mounted on, in or to base 44), and in particular opposite sides of translucent floor 86. A light beam (illustrated in the form of an arrow) is emitted from emitter 92 and is at least partially transmitted through the floor (e.g., floor 86) or the floor and fluid F and sensed by the detector 84. Optical sensor 90 may provide a signal to controller 38 when any amount of fluid is present in reservoir 32, or when a particular height of fluid is contained in reservoir 32.

In addition, non-contact sensor 34 may be used with other materials placed in reservoir 32, which materials may facilitate detection of fluid in reservoir 32. For example, reservoir 32 may include a compound that experiences a color change in the presence of the fluid, and sensor 34 may detect the color change of the material caused by the fluid, and generate a signal in response to the fluid as a consequence. The color-change material may be on a carrier (such as a piece of paper) that is affixed to the floor of reservoir 32.

As illustrated in FIG. 2 and discussed above, controller 38 is coupled to an indicator 36, one example of which is a light, such as a light emitting diode, and activates that indicator upon receipt of a signal from non-contact sensor 34. Indicator 36 may be used to provide an indication to the operator that the cycle should be terminated (manually by the operator) or will be terminated (automatically by controller 38) prior to the end of the normal cycle. Indicator 36 may take other forms of visible indicator, such as a display screen. Indicator 36 may also take the form of an audible indicator, such as a buzzer of other sound-producing element. Indicator 36 may be a haptic indicator, providing a tactile indication. Indicator 36 may be a combination of one or more of such visible, audible, haptic, etc. indicators.

While controller 38 may take the form of one or more electrical components or circuits, controller 38 comprises a processor and an associated memory according to one embodiment. According to such an embodiment, the processor may be programmed to carry out any of the actions that controller 38 is described as being configured to perform above. For example, the processor may be programmed to activate indicator 36 upon receipt of the signal from the sensor 34. The processor may also be programmed to deactivate light source 20 subsequent to receipt of the signal from sensor 34, and to deactivate agitator 30. The instructions by which the processor is programmed may be stored on the memory associated with the processor, which memory may include one or more tangible non-transitory computer readable memories, having computer executable instructions stored thereon, which when executed by the processor, may cause the one or more processors to carry out one or more actions.

As one example, the controller 38 may be programmed to carry out the following embodiment of a method of operating device 10, as explained with reference to the embodiment of irradiation device 10 illustrated in FIGS. 1, 2, and either FIGS. 3, 4 and 6 or FIGS. 5 and 7. It will be understood that the method may be carried out by other embodiments of the irradiation device 10 as well.

The method may begin with a determination whether the irradiation cycle should be initiated (step 110). For example, controller 38 may be coupled to a sensor disposed on housing, the sensor generating a signal when a biological fluid container 14 has been disposed in treatment chamber 12, and in particular in tray 50. Alternatively, the controller 38 may be coupled to an input device, such as a push button, that the user operates after biological fluid container 14 has been disposed in treatment chamber 12. In either event, controller 38 continues to monitor for a signal representative of the fact that the cycle should be initiated until such time as the signal is received.

Figure 8:
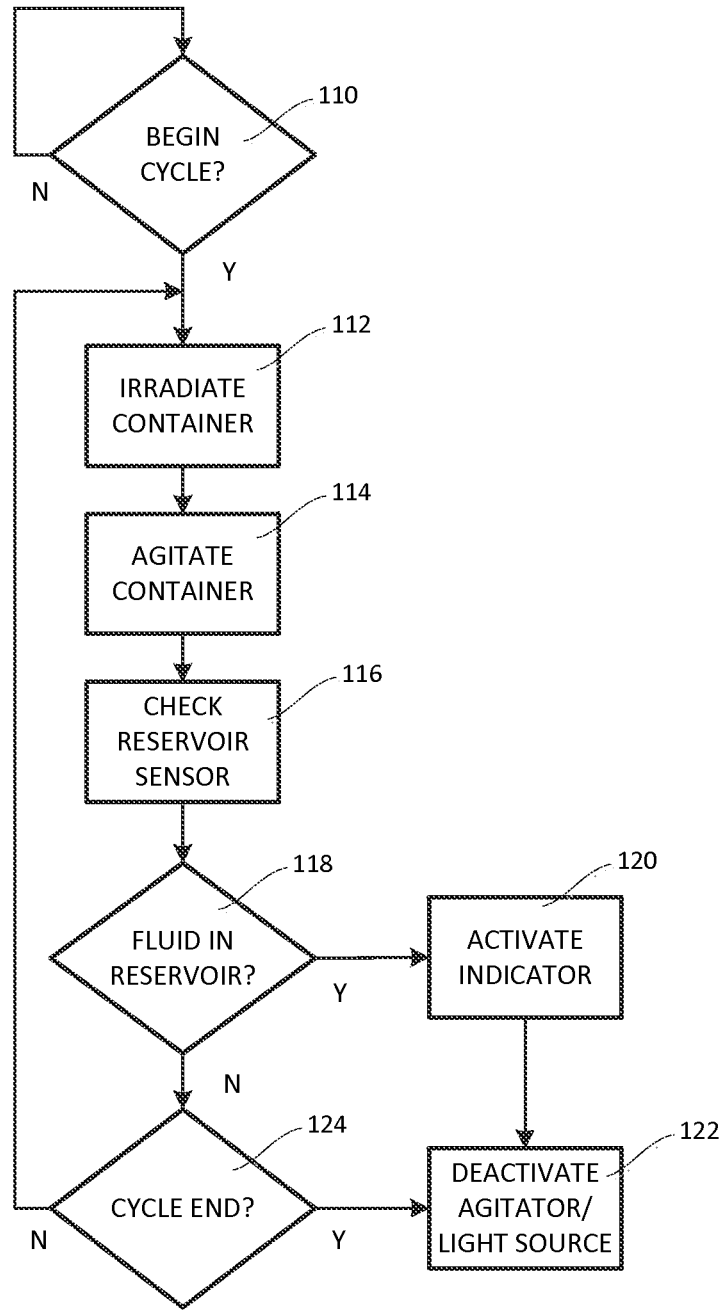
FIG. 8 is a flowchart of a method for using the sensors of FIGS. 6 and 7 with the trays of FIGS. 3-5 to control the operation of the device of FIG. 1.

Once controller 38 determines that the cycle should begin, controller 38 activates light source 20, thereby illuminating biological fluid container 14 in fluid treatment chamber 12 (step 112). According to certain embodiments, controller 38 may also activate agitator 30, thereby agitating biological fluid container 14 while biological fluid container 14 is illuminated (step 114). In more general terms, container 14 is illuminated and optionally agitated. While FIG. 8 illustrates that illumination (step 112) is initiated before agitation (step 114), this need not be the case according to all embodiments: initiation of agitation may precede illumination, or the two may be initiated as approximately the same time (i.e., "simultaneously").

The method continues with controller 38 checking sensor 34 (step 116) to determine if a signal has been received from non-contact sensor 34 disposed adjacent overflow reservoir 32 (step 118). The monitoring may occur simultaneously and in parallel with the illumination and the agitation of biological fluid container 14.

If controller 38 determines that a signal is received from sensor 34, controller 38 may then activate indicator 36 (step 120). According to certain embodiments, controller 38 activates indicator 36 upon receipt of a signal from the sensor 34, i.e., with little or no delay in activation of indicator 36 once the signal has been received. Controller 38 may also deactivate illumination (and optionally agitation) of biological fluid container 14 subsequent to sensing the biological fluid in overflow reservoir 32 (step 122). According to certain embodiments, controller 38 may deactivate the illumination and agitation of biological fluid container 14 automatically upon receipt of a signal from non-contact sensor 34, i.e., with little or no delay once the signal has been received and with no user input. As noted above, the deactivation of illumination and agitation may proceed in either order, or may occur simultaneously. Further, deactivation of illumination and agitation may occur before, after or simultaneous with the activation of indicator 36.

If controller 38 does not determine that a signal has been received from sensor 34, then controller 38 may determine if the normal cycle termination has occurred (step 124). For example, the illumination of biological fluid container 14 may occur only until a period of time has elapsed, or until the contents of biological fluid container have exposed to an amount of irradiation. The time period and irradiation exposure may be selected by the user, or device 10 may be configured to irradiate container 14 in amounts determined by the manufacturer of device 10. If the normal cycle has not been completed, then the method may continue to irradiate (and agitate) the container and monitor sensor 34 (steps 112, 114, 116, 118). After the cycle has been complete, controller 38 may deactivate light source 20 and agitator 30 (step 122).

In any event, after the controller deactivates light source 20 and agitator 30, the method may terminate, or controller 38 begin monitoring anew for a signal associated with the initiation of the cycle (step 110).

Figure 9:
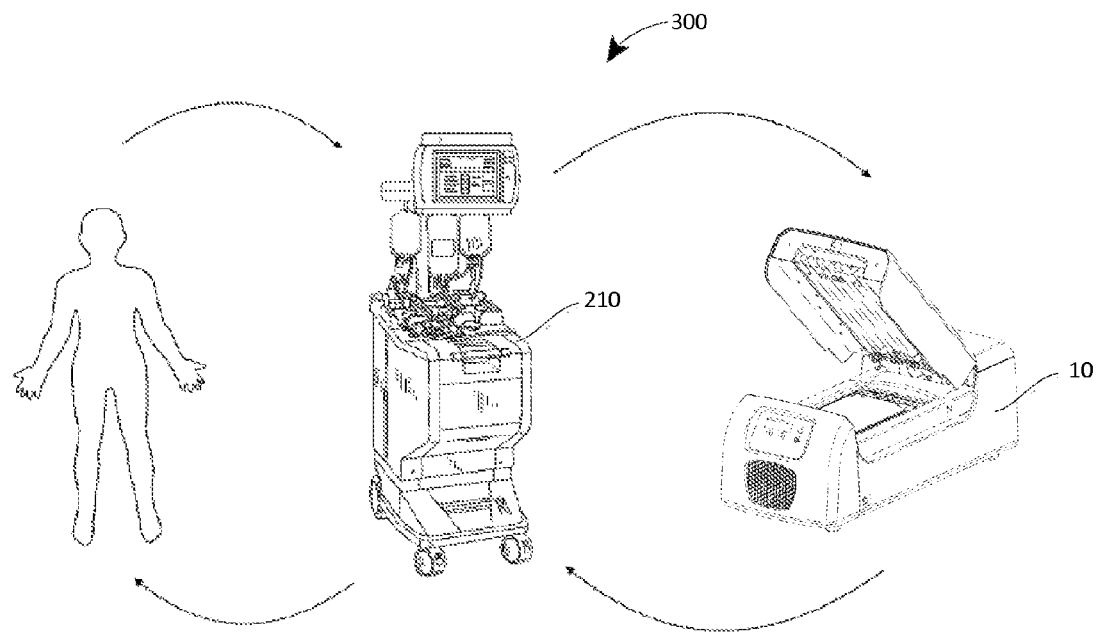
FIG. 9 is a diagram of an embodiment of a system including the irradiation device of FIG. 1 in combination with a cell separator.
Figure 10:
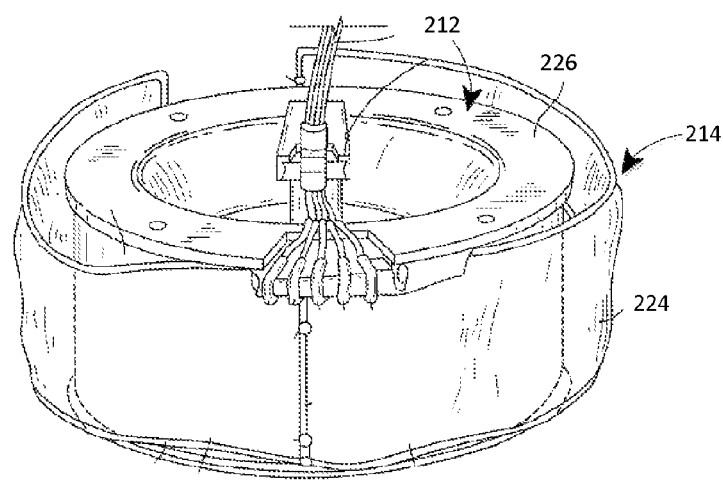
FIG. 10 is a perspective view of a processing container (separation chamber) of a processing set used with the separator of FIG. 9.
Figure 11:
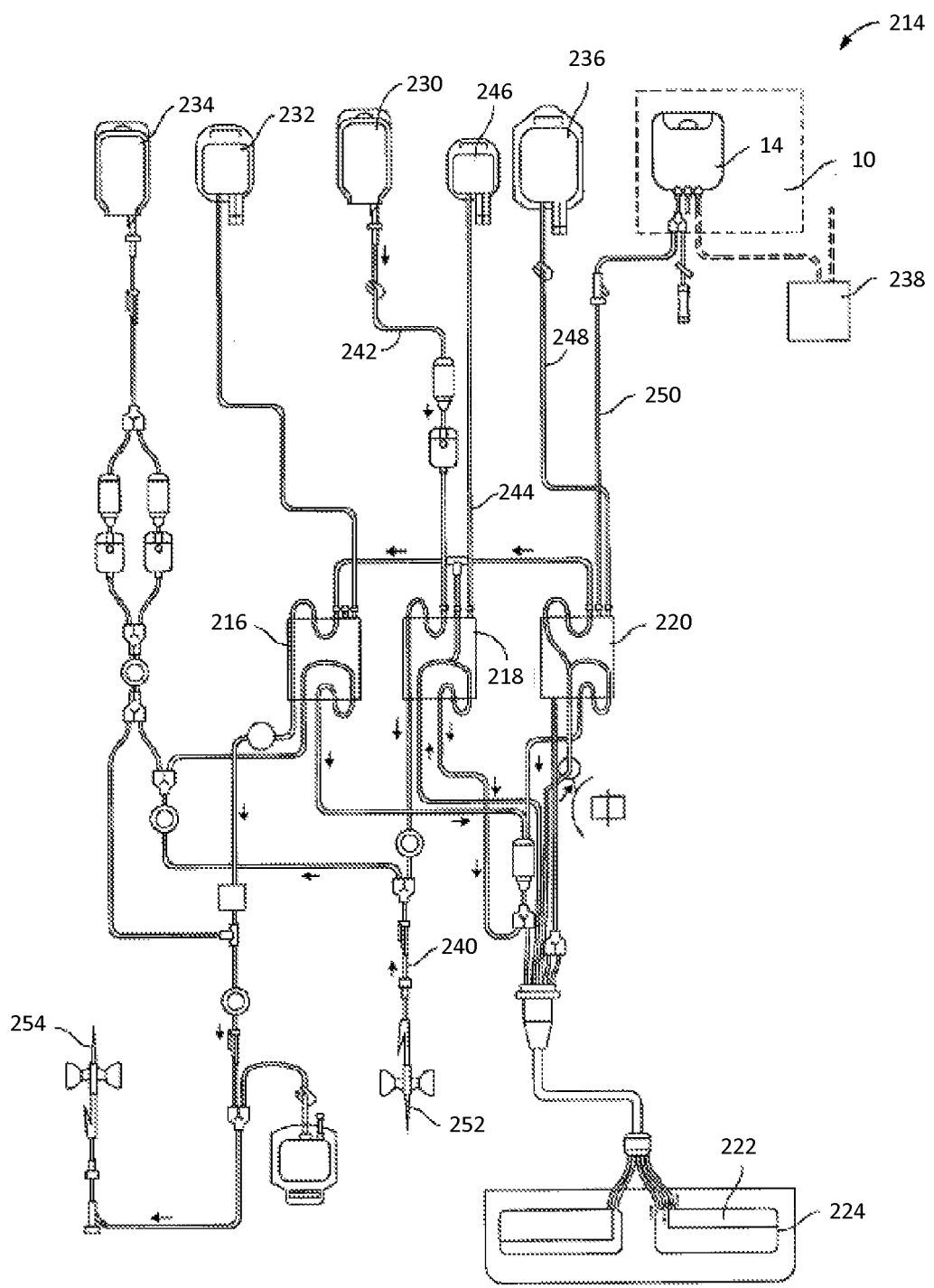
FIG. 11 is a diagram of a processing set for used with the separator of FIG. 9, including the biological fluid container of FIG. 1 and the processing container illustrated in FIG. 10.

While irradiation device 10 may be used as a stand-alone device, irradiation device 10 may also be used in conjunction with a cell separator 210 as part of a system 300, as illustrated in FIGS. 9-11.

According to system 300, the cell separator 210 would be configured to direct a biological fluid into a biological fluid container (e.g., container 14), and irradiation device 10 would include fluid treatment chamber 12 configured to receive biological fluid container 14, fluid treatment chamber 12 having opposing first and second sides 16, 18, light source 20 disposed adjacent at least one of first and second sides 16, 18 of fluid treatment chamber 12, overflow reservoir 32 in fluid communication with fluid treatment chamber 12 to receive fluid leaking from biological fluid container 14, non-contact sensor 34 disposed adjacent overflow reservoir 32 configured to generate a signal according to leaked fluid in overflow reservoir 32, indicator 36, and controller 38 coupled to light source 20, non-contact sensor 34 and indicator 36, controller 38 configured to activate indicator 36 upon receipt of the signal from sensor 34 and to deactivate light source 20 subsequent to receipt of the signal from sensor 34.

The cell separator 210 may be an Amicus® Separator made and sold by Fenwal, Inc., of Lake Zurich, Ill. Mononuclear cell collections performed using a device such as the Amicus® are described in greater detail in U.S. Pat. No. 6,027,657, the contents of which is incorporated by reference herein in its entirety. Briefly, FIGS. 9-11 show separator 210 in FIG. 9, a representative blood centrifuge 212 (defining part of the separator 210) with a portion of a fluid circuit 214 mounted thereon in FIG. 10, and the entire fluid circuit 214 in FIG. 11. Fluid circuit (also referred to as a processing set) 214 includes a plurality of processing fluid flow cassettes 216, 218 and 220 (see FIG. 11) with tubing loops for association with peristaltic pumps on device 210. Fluid circuit 214 also includes a network of tubing and pre-connected containers for establishing flow communication with the patient and for processing and collecting fluids and blood and blood components, as shown in greater detail in FIG. 11.

As illustrated in FIGS. 10 and 11, a separation chamber 222 is defined by the walls of a flexible processing container 224 carried within an annular gap defined by a rotating spool element 226 (see FIG. 10) and an outer bowl element (not shown). The processing container 224 takes the form of an elongated tube that is wrapped about the spool element 226 before use. The bowl and spool element 226 are pivoted on a yoke between an upright position and a suspended position, also not shown. In operation, the centrifuge 212 rotates the suspended bowl and spool element 226 about an axis, creating a centrifugal field within the processing chamber of container 224. Details of the mechanism for causing relative movement of the spool 226 and bowl elements as just described are disclosed in U.S. Pat. No. 5,360,542, the contents of which is also incorporated by reference herein in its entirety.

As seen in FIG. 11, the disposable processing set 214 may include flexible processing container 224, as well as a container 230 for supplying anticoagulant, a waste container 232 for collecting waste from one or more steps in the process for treating and washing mononuclear cells, a container 234 for holding saline or other wash or resuspension medium, a container 236 for collecting plasma, container 14 for collecting mononuclear cells from the operation discussed relative to FIG. 10 and, optionally, container 238 for holding a photoactivation agent.

Container 14 is preferably pre-attached to with the disposable set 214. Alternatively, container 14 may be attached to set 214 by known sterile connection techniques, such as sterile docking or the like. With reference to FIG. 11, fluid circuit includes inlet line 240, an anticoagulant (AC) line 242 for delivering AC from container 230, an RBC line 244 for conveying red blood cells from chamber 222 of container 224 to container 246, a platelet-poor plasma (PPP) line 248 for conveying PPP to container 236 and line 250 for conveying mononuclear cells to and from separation chamber 222 and collection/illumination container 14. The blood processing set 214 includes one or more venipuncture needle(s) for accessing the circulatory system of the patient. As shown in FIG. 11, fluid circuit 214 includes inlet needle 252 and return needle 254. In an alternative embodiment, a single needle can serve as both the inlet and outlet needle.

Container 14 is suitable for irradiation by light of a selected wavelength. By "suitable for irradiation", it is meant that the walls of the container are sufficiently translucent to light of the selected wavelength. In treatments using UVA light, for example, container walls made of ethylene vinyl acetate (EVA) are suitable. Accordingly, container 14 in which the mononuclear cells are collected may serve both as the collection container and the irradiation container. Container 14 may be placed inside irradiation device 10 by the operator or, more preferably, may be placed inside the irradiation chamber of irradiation device 10 at the beginning of a procedure including the cell separator and prior to whole blood withdrawal (as shown by the broken lines representing device 20 in FIG. 11). In any event, container 14 preferably remains integrally connected to the remainder of fluid circuit 214 during the entire procedure, thereby maintaining the closed or functionally closed condition of fluid circuit 214.

Fluid flow through fluid circuit 214 is preferably driven, controlled and adjusted by a microprocessor-based controller in cooperation with the valves, pumps, weight scales and sensors of device 210 and fluid circuit 214, the details of which are described in the previously mentioned U.S. Pat. No. 6,027,657.

Figure 12:
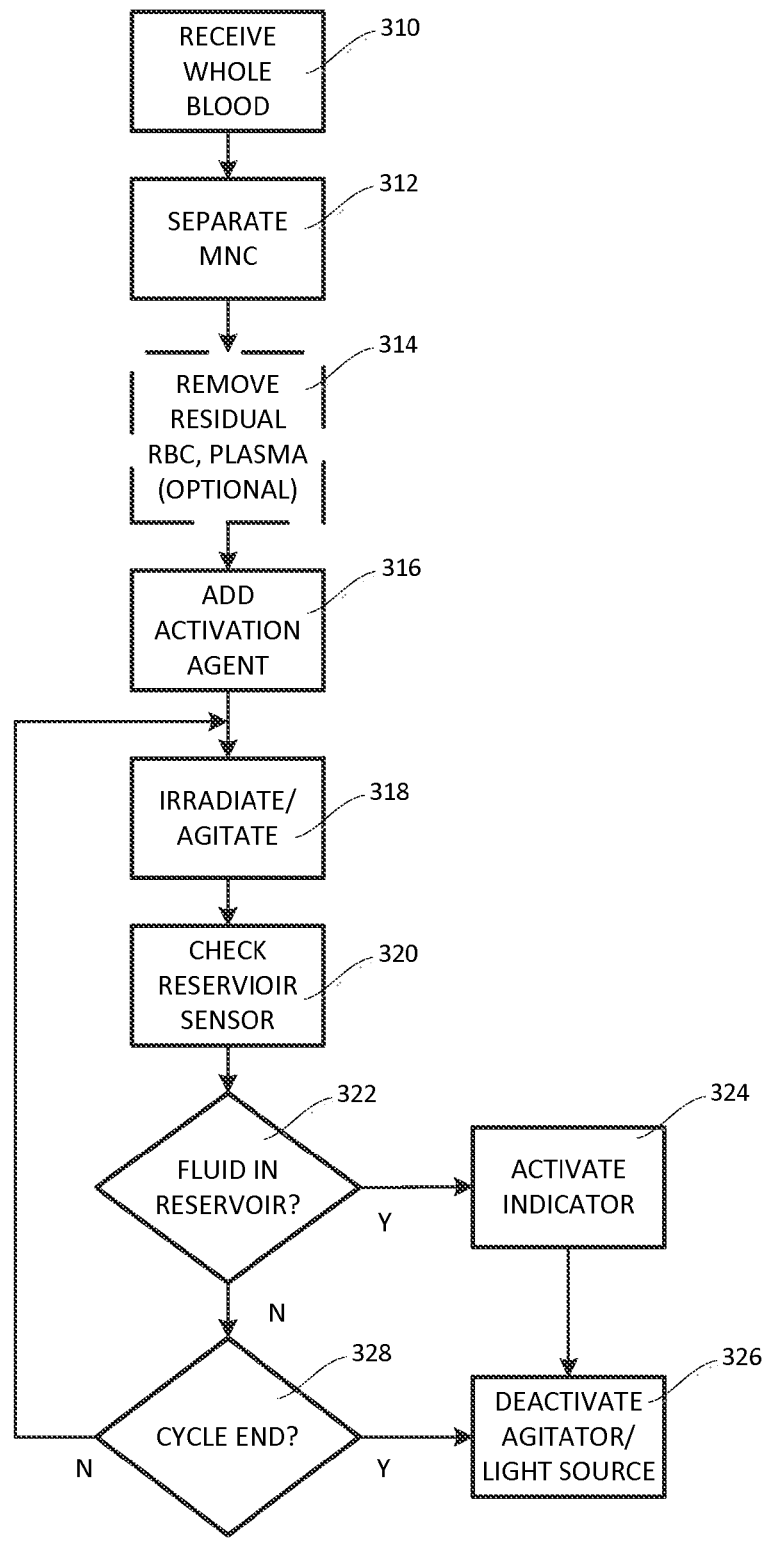
FIG. 12 is a flowchart of a method for using the system of FIGS. 9-11.

The system 300 may be used for the treatment of mononuclear cells with ultraviolet light as illustrated in FIG. 12. First, separator 210 receives whole blood that has been withdrawn from a patient (step 310). The whole blood is introduced into separation chamber 222 of separator 210, where the whole blood is subjected to a centrifugal field. The centrifugal field separates the target cell population, i.e., mononuclear cells (MNC), from red blood cells (RBC), platelets and plasma (step 312). The red blood cells and platelets separated at this stage may be returned to the patient, or optionally may be diverted to a container (e.g., container 246) for further processing.

As a practical matter, a quantity of red blood cells and plasma typically remains in suspension with the separated mononuclear cells. These red blood cells and plasma may be optionally removed prior to further processing (step 314). The removal of the residual red blood cells and plasma can have the effect of reducing irradiation time from, for example, approximately 30 minutes to approximately 5 minutes.

According to different embodiments of the method of treating mononuclear cells with ultraviolet light described herein, different methods for removing the residual red blood cells and plasma may be used when this action is optionally included. For example, according to one embodiment, a lysing agent is added to the suspended mononuclear cells, and then the suspension is incubated to activate the lysing agent to disintegrate or dissolve the red blood cells. The suspension is then washed using separator 210 to remove plasma and hemoglobin freed by the lysis of the red blood cells. The washed, lysed suspension is then re-suspended. Alternatively, the residual red blood cells may be removed from the MNC suspension by using immunogenic cell separation techniques, in which paramagnetic beads coated with antibodies are used to bind the beads to antigens on the surface of the red blood cells, and the suspension is subjected to a magnetic force to separate the red blood cells, or additional density gradient separation (using, e.g., the centrifuge) may be performed.

In any event, the MNC suspension is subsequently combined with an activation agent (step 316), and then exposed to ultraviolet light (step 318) with the intent to obtain a treated cell product. In one non-limiting example, during treatment, the mononuclear cell product may be exposed to UV bulbs having a wavelength in the UVA range of about 320 nm to 400 nm for a selected period of time, preferably 5 minutes or less, resulting in an average UVA exposure of approximately 0.5-5.0 $J/cm^2$. As indicated, the container in which the MNC suspension and activation agent may also be moved to agitate the contents.

As explained above relative to FIG. 8, the container in which the MNC suspension is disposed (i.e., biological fluid container 14) is checked for leakage during operation of device 10. In particular, non-contact sensor 34 may be used to check or monitor overflow reservoir 32 to determine if the contents are leaking from container 14 (step 320). If the determination is made that there is fluid in reservoir 32 (step 322) associated with possible leakage of contents from container 14, then indicator 36 may be activated (step 324) and light source 20 (and optionally agitator 30) may be deactivated (step 326). It will be recognized that as a consequence, the operation of device 10 may be terminated even though the entire operational cycle has not been completed. Alternatively, if the determination is made that no fluid is sensed or detected in reservoir 32, then the operation of device 10 will continue until such time as the operational cycle is at an end (step 328) at which point light source 20 (and agitator 30) may be deactivated (step 326). The comments in regard to the method illustrated in FIG. 8 apply with equal force to the method illustrated in FIG. 12, for example, as regarding the sequencing of different actions relating to the activation and deactivation of light source 20 and agitator 30.

Assuming that the cycle is not terminated prior to the end of the normal operational cycle, the treated cell product is then returned to the patient. Optionally, again assuming that the cycle is not terminated prior to the end of the normal operational cycle, the treated mononuclear cells may first be returned to separator 210 and concentrated to provide for the concentrated cells to have a smaller total volume as compared to un-concentrated cells. As a result, the smaller volume of concentrated MNCs may be more quickly reinfused to a patient.

Automated control of the MNC collection and the irradiation treatment may be affected by the microprocessor-based controller of the respective separation device 210 and irradiation device 10 with some operator input for each device. Alternatively, operation of both separation device 210 and irradiation device 10 and the process steps carried out by each may be remotely controlled by a separate controller (e.g., a computer) that communicates with both.

Without limiting any of the foregoing, the disclosed device, method and system may include one or more of the aspects set forth below.

In a first aspect, an irradiation device includes a fluid treatment chamber configured to receive a biological fluid container, the fluid treatment chamber having opposing first and second sides, at least one light source disposed adjacent at least one of the first and second sides of the fluid treatment chamber, and an overflow reservoir in fluid communication with the fluid treatment chamber to receive fluid leaking from the biological fluid container. The irradiation device also includes a non-contact sensor disposed adjacent the overflow reservoir and configured to generate a signal according to leaked fluid in the overflow reservoir, an indicator, and a controller coupled to the at least one light source, the non-contact sensor and the indicator, the controller configured to activate the indicator upon receipt of the signal from the sensor and to deactivate the at least one light source subsequent to receipt of the signal from the sensor.

In another aspect, the irradiation device includes an agitator coupled to the fluid treatment chamber to move the fluid treatment chamber with an oscillatory motion, the controller coupled to the agitator and configured to deactivate the agitator subsequent to receipt of the signal from the sensor.

In a further aspect, the irradiation device includes a tray, the tray having a first recess defining the fluid treatment chamber and a second recess defining at least in part the overflow reservoir. The tray may have a lip that separates the first recess from the second recess. The tray may have a first end and a second end, the second recess disposed at the first end of the tray. The tray may have a third recess, the third recess disposed at the second end of the tray, and the second and third recesses defining the overflow reservoir. The first recess has a translucent floor, and the second (and third) recess may have a translucent or a non-translucent floor.

In still further aspect, the non-contact sensor is an optical sensor, such as a reflective light sensor or a light absorption sensor. A reflective light sensor may include a light emitter and a light detector, the light emitter and light detector both disposed on one side of the overflow reservoir. A light absorption sensor may include a light emitter and a light detector, the overflow reservoir having a translucent floor, the light emitter and the light detector disposed on opposite sides of the overflow reservoir.

In yet another aspect, the controller is configured to automatically deactivate the at least one light source upon receipt of the signal from the overflow reservoir. The controller may include a processor and memory, and the processor may be programmed to activate the indicator upon receipt of the signal from the overflow reservoir and to deactivate the at least one light source subsequent to receipt of the signal from the overflow reservoir.

In a related aspect, a method of controlling an irradiation device includes Illuminating a biological fluid container in a fluid treatment chamber, sensing biological fluid from the fluid container in overflow reservoir in fluid communication with the fluid treatment chamber using a non-contact sensor, activating an indicator after sensing the biological fluid in the overflow reservoir, and deactivating illumination of the biological fluid container subsequent to sensing the biological fluid in the overflow reservoir.

In another aspect, the method may include automatically deactivating illumination of the biological fluid container subsequent to sensing the biological fluid in the overflow reservoir. Where the method includes agitating the biological fluid container while illuminating the biological fluid container, the method may include deactivating agitation of the biological fluid container subsequent to sensing the biological fluid in the overflow reservoir. In fact, the method may include automatically deactivating agitation of the biological fluid container subsequent to sensing the biological fluid in the overflow reservoir.

In a further aspect, the method may include sensing biological fluid from the fluid container in overflow reservoir in fluid communication with the fluid treatment chamber using an optical sensor.

In another related aspect, a system includes a cell separator configured to direct a biological fluid into a biological fluid container and an irradiation device. The irradiation device is configured according to any one, or combinations, of the aspects above, or configured to perform the methods of any one, or combinations, of the aspects above.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description, but is set forth in the following claims.

The invention claimed is:

1. An irradiation device comprising:
   a fluid treatment chamber configured to receive a biological fluid container, the fluid treatment chamber having opposing first and second sides;
   at least one light source disposed adjacent to at least one of the first and second sides of the fluid treatment chamber;
   an overflow reservoir in fluid communication with the fluid treatment chamber to receive fluid leaking from the biological fluid container;
   a non-contact sensor disposed adjacent to the overflow reservoir and configured to generate a signal according to leaked fluid in the overflow reservoir;
   an indicator; and a controller coupled to the at least one light source, the non-contact sensor and the indicator, the controller configured to activate the indicator upon receipt of the signal from the sensor and to deactivate the at least one light source subsequent to receipt of the signal from the sensor.

2. The irradiation device of claim 1, further comprising:
an agitator coupled to the fluid treatment chamber to move the fluid treatment chamber with an oscillatory motion,
the controller coupled to the agitator, the controller configured to deactivate the agitator subsequent to receipt of the signal from the sensor.

3. The irradiation device of claim 1, further comprising a tray, the tray having a first recess defining the fluid treatment chamber and a second recess defining at least in part the overflow reservoir, the first recess having a translucent floor.

4. The irradiation device of claim 3, wherein the tray has a lip that separates the first recess from the second recess.

5. The irradiation device of claim 3, wherein the tray has a first end and a second end, the second recess disposed at the first end of the tray.

6. The irradiation device of claim 5, wherein the tray has a third recess, the third recess disposed at the second end of the tray, and the second and third recesses defining the overflow reservoir.

7. The irradiation device of claim 6, wherein the second and third recesses each have a translucent floor.

8. The irradiation device of claim 3, wherein the second recess has a translucent floor.

9. The irradiation device of claim 1, wherein the non-contact sensor is an optical sensor.

10. The irradiation device of claim 9, wherein the optical sensor is one of a reflective light sensor and a light absorption sensor.

11. The irradiation device of claim 10, wherein the non-contact sensor is a reflective light sensor comprising a light emitter and a light detector, the light emitter and light detector both disposed on one side of the overflow reservoir.

12. The irradiation device of claim 10, wherein the non-contact sensor is a light absorption sensor comprising a light emitter and a light detector, the overflow reservoir having a translucent floor, the light emitter and the light detector disposed on opposite sides of the overflow reservoir.

13. The irradiation device of claim 1, wherein the controller is configured to automatically deactivate the at least one light source upon receipt of the signal from the overflow reservoir.

14. The irradiation device of claim 1, wherein the controller comprises a processor and memory, and the processor is programmed to activate the indicator upon receipt of the signal from the overflow reservoir and to deactivate the at least one light source subsequent to receipt of the signal from the overflow reservoir.

15. A system comprising:
a cell separator configured to direct a biological fluid into a biological fluid container; and
an irradiation device comprising:
a fluid treatment chamber configured to receive the biological fluid container, the fluid treatment chamber having opposing first and second sides;
at least one light source disposed adjacent to at least one of the first and second sides of the fluid treatment chamber;
an overflow reservoir in fluid communication with the fluid treatment chamber to receive fluid leaking from the biological fluid container;
a non-contact sensor disposed adjacent to the overflow reservoir and configured to generate a signal according to leaked fluid in the overflow reservoir;
an indicator; and
a controller coupled to the at least one light source, the non-contact sensor and the indicator, the controller configured to activate the indicator upon receipt of the signal from the sensor and to deactivate the at least one light source subsequent to receipt of the signal from the sensor.

16. A method of controlling an irradiation device, the method comprising:
Illuminating a biological fluid container in a fluid treatment chamber of the irradiation device of claim 1;
sensing biological fluid from the fluid container in overflow reservoir in fluid communication with the fluid treatment chamber using a non-contact sensor;
activating an indicator after sensing the biological fluid in the overflow reservoir; and
deactivating illumination of the biological fluid container subsequent to sensing the biological fluid in the overflow reservoir.

17. The method of claim 16, wherein deactivating illumination of the biological fluid container comprises automatically deactivating illumination of the biological fluid container subsequent to sensing the biological fluid in the overflow reservoir.

18. The method of claim 17, further comprising:
agitating the biological fluid container while illuminating the biological fluid container; and
deactivating agitation of the biological fluid container subsequent to sensing the biological fluid in the overflow reservoir.

19. The method of claim 18, wherein deactivating agitation of the biological fluid container comprises automatically deactivating agitation of the biological fluid container subsequent to sensing the biological fluid in the overflow reservoir.

20. The method of claim 16, wherein sensing biological fluid from the fluid container in overflow reservoir comprises sensing biological fluid from the fluid container in overflow reservoir in fluid communication with the fluid treatment chamber using an optical sensor.

* * * * *